United States Patent [19]

Duffett

[11] Patent Number: Plant 5,984

[45] Date of Patent: May 12, 1987

[54] CHRYSANTHEMUM PLANT NAMED KARMA

[75] Inventor: William E. Duffett, Salinas, Calif.

[73] Assignee: Yoder Brothers, Inc., Barberton, Ohio

[21] Appl. No.: 765,517

[22] Filed: Aug. 14, 1985

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Karma having flat capitulum form; daisy capitulum type; white ray floret color; diameter across face of capitulum ranging from 5.5 to 7.0 cm. at maturity; uniform eight week photoperiodic flowering response to short days; medium plant height when grown as a pinched spray pot mum; semi-spreading branching pattern; tolerance of both low winter 12° C. to 13° C. and high summer 23° C. to 38° C. temperatures for bud initiation and flower development; and intense green, pollen-free disc florets.

3 Drawing Figures

The present invention comprises a new and distinct cultivar of *Chrysanthemum morifolium,* Ramat., named Karma.

Karma is a product of a planned breeding program which had the objective of creating new Chrysanthemum cultivars for pinched spray pot mum programs having daisy capitulum type, white ray floret color, eight week flowering response, and the ability to produce commercially acceptable quality in year round programs. Such traits in combination were not present or required improvements in previously available commercial cultivars.

Karma, identified as 82007010, was originated from a cross made in a controlled breeding program in Salinas, Calif. in 1981. The female parent of the stated cross was an unnamed seedling, identified as 79F54008. The male parent of the stated cross was an unnamed seedling, identified as 80100001.

Karma was discovered and selected as one flowering plant within the progeny of the stated cross by William E. Duffett in September 1982 in a controlled environment in Salinas, Calif.

The first act of asexual reproduction of Karma was accomplished when vegetative cuttings were taken from the initial selection in December 1982 in a controlled environment in Salinas, Calif. by a technician working under formulations established and supervised by William E. Duffett. Horticultural examination of selected units initiated April 1983 has demonstrated that the combination of characteristics as herein disclosed for Karma are firmly fixed and are retained through successive generations of asexual reproduction.

Karma has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Karma which in combination distinguish this Chrysanthemum as a new and distinct cultivar:

(1) Flat capitulum form.

(2) Daisy capitulum type.

(3) White ray floret color.

(4) Diameter across face of capitulum ranging from 5.5 to 7.0 cm. at maturity.

(5) Uniform eight week photoperiodic flowering response to short days.

(6) Medium plant height, requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots.

(7) Semi-spreading branching pattern.

(8) Tolerance of low winter 12° C. to 14° C. temperatures.

(9) Tolerance of high summer 23° C. to 38° C. temperatures.

(10) Intense green, pollen-free disc florets.

The accompanying photographic drawings depict typical leaf and inflorescence characteristics of Karma.

Sheet 1 is a color photograph of a plant of Karma grown as a pinched spray pot mum, with colors being as accurate as possible with renditions of this type.

Sheet 2 is a black and white photograph of three views of the inflorescence of Karma.

Sheet 3 shows the leaves of Karma in three stages of growth (mature, intermediate and immature).

Of the many commercial cultivars known to the present inventor the most similar in comparison to Karma is Garland, disclosed in U.S. Plant Pat. No. 3,576. Reference is made to attached Chart A which compares certain characteristics of Karma to those same characteristics of Garland.

Similar traits are type, form, color and pollen-free disc florets. Karma has smaller foliage, a short, more spreading plant habit, faster response time, smaller capitulum diameter, shorter ray floret length, and its tolerance of both high and low temperatures results in more rapid and more uniform response under high and low temperatures, respectively.

In the following description, color references are made to The Royal Horticultural Society Colour Chart. The color values were determined between 9:30 and 9:45 a.m. on Nov. 28, 1984 under 380 foot-candle light intensity at Salinas, Calif.

Classification:

*Botanical.*—*Chrysanthemum morifolium,* Ramat., cv Karma.

*Commercial.*—Daisy spray pot mum.

I. INFLORESCENCE

A. Capitulum:

*Form.*—Flat.

*Type.*—Daisy.

*Diameter across face.*—5.5 to 7.0 cm.

B. Corolla of ray florets:

*Color (general tonality from a distance of three meters).*—White.

*Color (upper surface).*—155D.

*Color (under surface).*—155D.

*Shape.*—Short. Narrow with pointed tip.

C. Corolla of disc florets:

*Color (mature).*—154C and 150C.

*Color (immature).*-5B.

D. Reproductive organs:

*Androecium.*—Present disc florets only; no pollen.

*Gynoecium.*—Present both ray and disc florets.

II. PLANT

A. General appearance:

*Height.*—medium.

*Branching pattern.*—Semi-spreading.

B. Foliage:

*Color (upper surface).*—147A.

*Color (under surface).*—147B.

*Shape.*—Deeply lobed. Smooth but deep serration.

CHART A

COMPARISON OF KARMA AND GARLAND

| RAY | CAPITULUM |
|---|---|

CHART A-continued

COMPARISON OF KARMA AND GARLAND

| CULTIVAR | FLORET COLOR | FORM AND TYPE | BRANCHING PATTERN |
|---|---|---|---|
| KARMA | WHITE | FLAT DAISY | SEMI SPREADING |
| GARLAND | WHITE | FLAT DAISY | SEMI UPRIGHT |

| CULTIVAR | DIAMETER ACROSS FACE OF CAPITULUM | PLANT HEIGHT | FLOWERING RESPONSE PERIOD | TEMPERATURE TOLERANCE |
|---|---|---|---|---|
| KARMA | 5.5 to 7.0 cms. | MEDIUM | 8 WEEKS | LOW: 12° C. to 14° C. HIGH 23° C. to 38° C. |
| GARLAND | 7 to 9 cms. | TALL | 9 WEEKS | LOW: 13° C. to 14° C. HIGH: 18° C. to 22° C. |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Karma, as described and illustrated, and particularly characterized as to uniqueness by the combined characteristics of flat capitulum form; daisy capitulum type; white ray floret color; diameter across face of capitulum ranging from 5.5 to 7.0 cm. at maturity; uniform eight week flowering response; medium plant height; semi-spreading branching pattern; tolerance of both low winter 12° C. to 13° C. and high summer 23° C. to 38° C. temperatures for bud initiation and flower development; and intense green, pollen-free disc florets.

* * * * *

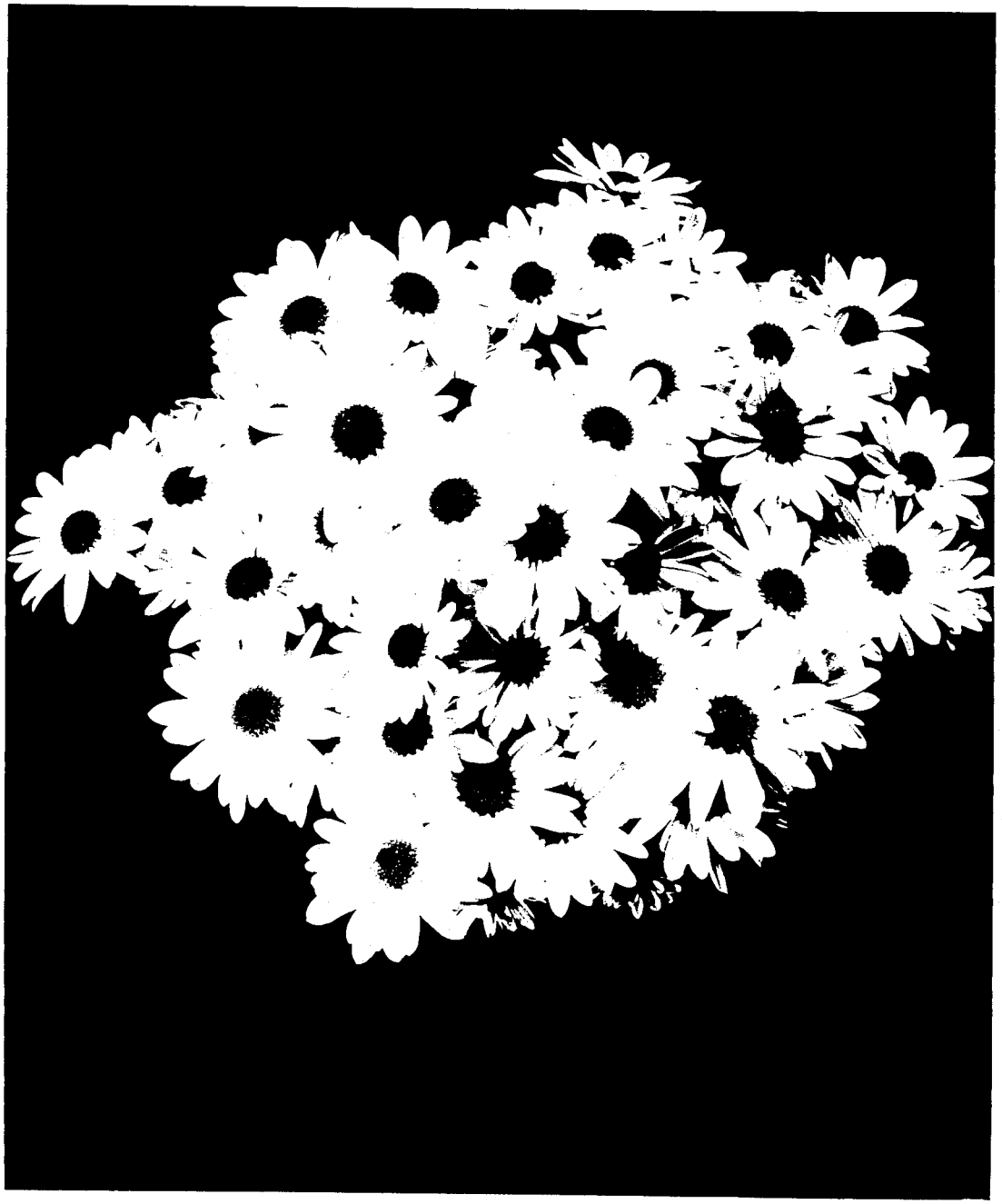

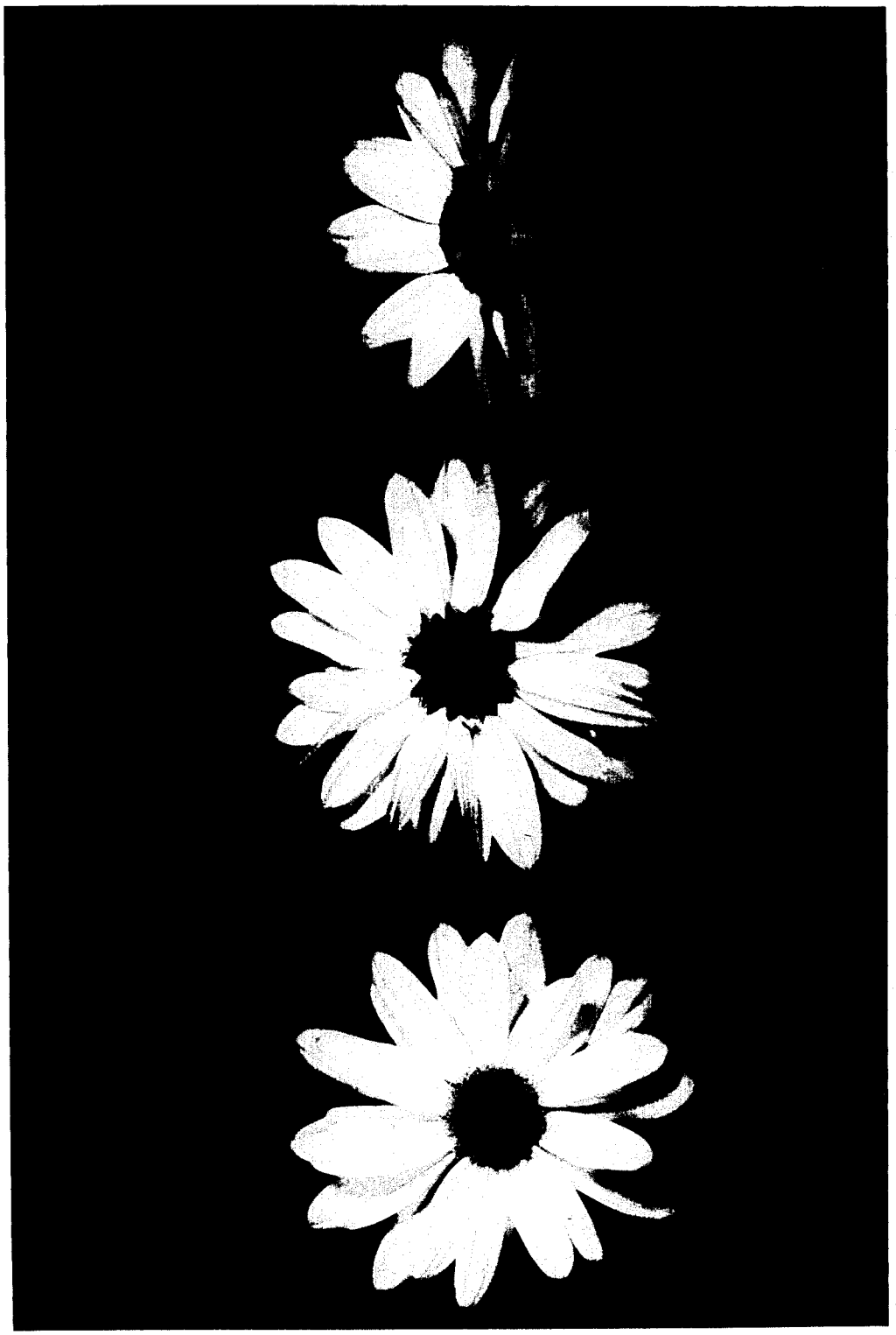

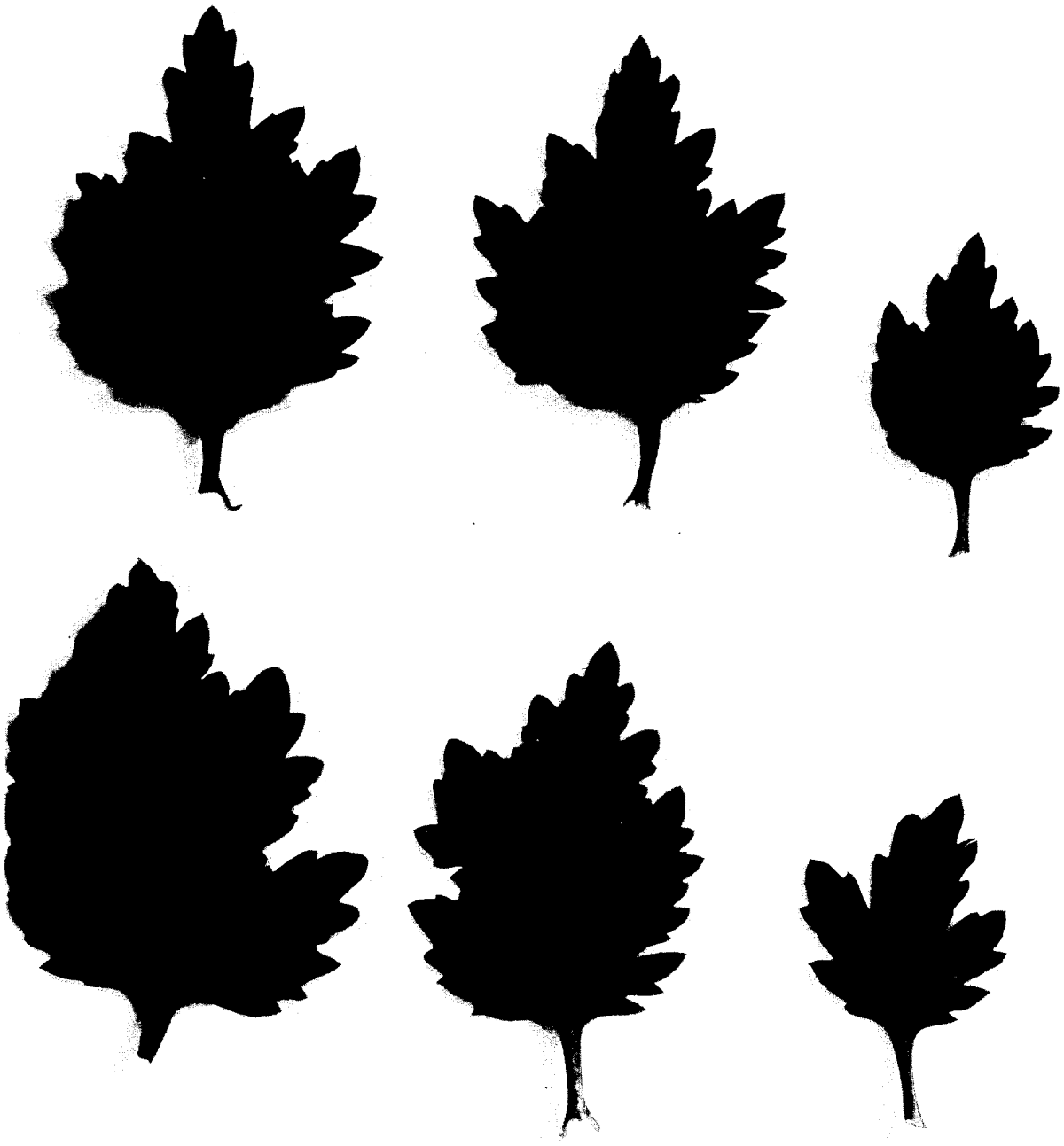

UNITED STATES PATENT AND TRADEMARK OFFICE

CERTIFICATE OF CORRECTION

PATENT NO. : PP 5,984

DATED : May 12, 1987

INVENTOR(S) : William E. Duffett

It is certified that error appears in the above-identified patent and that said Letters Patent is hereby corrected as shown below:

In Column 3, line 21 should read:

"Color (immature). --145B"

Signed and Sealed this

Fourteenth Day of November, 1989

*Attest:*

JEFFREY M. SAMUELS

*Attesting Officer*

*Acting Commissioner of Patents and Trademarks*